United States Patent [19]

Hungerford et al.

[11] Patent Number: 5,091,863

[45] Date of Patent: Feb. 25, 1992

[54] AUTOMATIC FLUID SAMPLING AND FLOW MEASURING APPARATUS AND METHOD

[75] Inventors: William G. Hungerford, Medina; Donald Miller; Carl Griffith, both of Middleport; Donald Kaiser, Tonawanda, all of N.Y.

[73] Assignee: American Sigma, Inc., Medina, N.Y.

[21] Appl. No.: 455,981

[22] Filed: Dec. 22, 1989

[51] Int. Cl.$^5$ .................. G01F 11/00; B65B 3/00
[52] U.S. Cl. .................. 364/510; 73/863.01; 141/1
[58] Field of Search .......... 364/510; 141/130, 94, 141/91, 89, 1; 73/863.03, 863.02, 863.01, 863, 864.34

[56] References Cited

U.S. PATENT DOCUMENTS

| | | | |
|---|---|---|---|
| 3,507,156 | 2/1968 | Merrill, Jr. | 73/863.02 |
| 3,727,464 | 4/1973 | Rutkowski et al. | 73/863.01 |
| 3,838,719 | 10/1974 | Lederer | 141/284 |
| 3,927,701 | 12/1975 | Lederer | 141/98 |
| 3,929,017 | 12/1975 | Kowalski | 364/510 X |
| 3,996,786 | 12/1976 | Mead et al. | 73/53 X |
| 4,022,059 | 5/1977 | Schontzler et al. | 141/130 X |
| 4,660,422 | 4/1987 | Eads et al. | 73/863.02 |
| 4,660,607 | 4/1987 | Griffith et al. | 141/1 |
| 4,697,462 | 10/1987 | Daube, Jr. et al. | 73/862.02 X |
| 4,766,550 | 8/1988 | Byers et al. | 73/863.01 X |
| 4,799,169 | 1/1989 | Mims | 73/510 |

*Primary Examiner*—Thomas G. Black
*Assistant Examiner*—S. A. Melnick
*Attorney, Agent, or Firm*—Irving M. Weiner; Joseph P. Carrier; Pamela S. Burt

[57] ABSTRACT

An automatic liquid sampling and flow measuring apparatus provided as a unitary structure within a case, and capable of collecting liquid samples at selected intervals, measuring flow rate through a channel at selected intervals, and collecting and storing sampling and flow rate data for later retrieval. The apparatus is provided with its own self-contained microprocessor for automatically controlling sampling operations, calculating flow rate on the basis of signals from a sensor, and storing data relating to sample collection and flow rate measurement. The stored data can be called up on a display of the apparatus, or can be transferred via a portable transfer unit to an external output device, such as a printer capable of producing a hard copy of the data.

36 Claims, 13 Drawing Sheets

AUTOMATIC FLUID SAMPLING AND FLOW MEASURING APPARATUS AND METHOD

BACKGROUND OF THE INVENTION

1. Field of the Invention

The present invention relates generally to an integrated automatic fluid sampling and flow measuring apparatus having a compact unitary structure and capable of pacing sampling in proportion to flow rate. More particularly, the invention relates to a unitary fluid sampling and flow measuring apparatus provided with a computer control system for automatically computing flow rate, controlling sampling operations in proportion to time and/or flow volume and/or flow rate, and monitoring and storing flow rate and sample collection data for later retrieval by a user. The stored data can be retrieved by displaying same on an alphanumeric display built into the apparatus, and/or by transferring the data via a portable data transfer unit according to the invention to a remote output device such as a printer and/or a personal computer.

2. Description of the Relevant Art

Mounting concerns over environmental pollution, and legislation enacted to limit the discharge of industrial effluent, have caused municipal water pollution agencies to carefully monitor the composition and volume of wastewater discharged from industrial concerns. Typically, an automatic liquid sampling apparatus is used to monitor the composition of fluid waste by repeatedly collecting samples for subsequent analysis, together with a separate flowmeter for monitoring the volume of flow and pacing the sampler in proportion to flow rate. The sampler and flowmeter are regularly transported to the field for temporary set up, or left in a place permanently, to monitor a sewer line containing industrial discharge.

Various problems arise in transporting and mounting the sampler and flowmeter for use in a sewer manhole. First, sampling sites are frequently remote, so that transporting the two separate devices is cumbersome and inconvenient. Moreover, positioning and mounting of the two devices as well as the associated sampler intake and flow transducer within a manhole often proves to be difficult and sometimes impossible due to the close confines of the sewer manhole, which severely restricts manipulation of the devices for positioning and later retrieval. Past practice has frequently dictated that the separate sampler and flowmeter be suspended one over the other from a manhole ladder or other support means. Typically, the operator first enters the manhole to position the flow transducer and sampler intake line. Next he exits the manhole to retrieve the flowmeter, re-enters the manhole, and then suspends or otherwise positions the flowmeter. Once done, he must exit again to retrieve the sampler and then re-enter the manhole to position the sampler.

Problems also arise in access to and removal of the separate sampler and flowmeter. Once in place, the sampler typically blocks access to the flowmeter, or vice versa. If access to the lower of the two units is needed, the unit above must be removed first. Removal of the units after monitoring is completed is often as awkward and time consuming as mounting them.

Another critical problem which arises with presently known samplers is the inability to obtain a hard copy of sample collection data, e.g., times and dates of collected and/or missed samples and parameters of the sampling program such as the volume of the collected sample, the interval between samples, and time or flow units remaining until the next sample. To comply with federal and state requirements, it is important that a record be kept of sample collection and flow rate data. With known sampler devices, the only means by which such a record can be obtained is by recording the data by hand when it appears temporarily on a display of the device. This limitation leads to inaccurate or incomplete records at best, and no hard copy of the data at worst.

Known systems which use an automatic fluid sampler in conjunction with a flowmeter have failed to overcome the foregoing problems. Although some of these systems provide for electrical connection between the sampler and the flowmeter to permit flow proportional sampling, they fail to overcome the positioning and mounting problems described above because they rely on two separate monitoring devices, each of which must be separately positioned and mounted within a manhole. An example of such a known system is that disclosed in U.S. Pat. No. 4,022,059 issued in 1977 to Schontzler et al.

The fluid sampling device disclosed for use in the system of U.S. Pat. No. 4,022,059 represents one of various known types of sampling devices. In U.S. Pat. No. 4,022,059 the sampling device is provided with a sample collection chamber in which a vacuum is generated to draw a sample into the chamber, after which the sample is deposited in a storage container. Other known sampling devices are disclosed in U.S. Pat. No. 3,838,719 issued in 1974 to Lederer and U.S. Pat. No. 3,927,701 issued in 1975 to Lederer.

Another known fluid sampling device is disclosed in U.S. Pat. No. 4,660,607 issued in 1987 to Griffith et al. The device includes a reversible, positive displacement pump having a tube passing therethrough which extends from a fluid supply at one end to a sample collector at the other end. The pump is cyclically operated in a reverse purging direction or a forward sample drawing direction depending on signals supplied by a processor. The processor determines the rate of liquid flow and the time the pump must operate to fill the entire tube plus a desired sample volume on the basis of signals from a fluid detection sensor disposed upstream of the pump inlet, and user programmed data relating to an intake portion of the tube. Advantages afforded by such device over other known samplers include reliability, minimized power consumption, contact of the sample liquid by the tube only, and minimization of any effect on sample volume by changes in vertical lift, power supply voltage or motor RPM.

Known devices or systems for monitoring the volume of fluid flow include those disclosed in U.S. Pat. No. 3,866,018 issued in 1975 to Schontzler et al and U.S. Pat. No. 3,929,017 issued in 1975 to Kowalski.

The present invention overcomes the problems encountered in the use of known fluid samplers and flowmeters as separate monitoring devices by providing an integrated automatic liquid sampling and flow measuring apparatus having a compact unitary structure and capable of pacing sampling in proportion to flow rate. Positioning and mounting of the unitary structure within a manhole is greatly simplified relative to having to position and mount two separate monitoring devices as has heretofore been required. The compact unitary structure of the invention also simplifies positioning of sample intake tubes and flow transducers, as well as rendering transport of the equipment to a remote site more convenient.

The invention also provides means for storing both sample collection and flow data for retrieval in hard copy form, which has heretofore been impossible with known devices.

The integrated apparatus of the invention includes computer control means for automatically computing flow rate, controlling sampling operations on the basis of the flow rate and/or time, and monitoring and storing flow and sample collection data. Access to flow and sample collection data can be had via an alphanumeric display mounted integrally to the unit itself. Unlike any other known system, the invention also provides a portable pocket-sized data transfer unit for retrieving data stored in the unit's computer control means for transfer to a remote output device such as a conventional printer and/or computer. As such, the invention provides convenient means for obtaining a hard copy of the data; storing the data in a remote computer data base; or manipulating the data for statistical analyses, spreadsheeting or the like by a conventional computer provided with a suitable software program.

SUMMARY OF THE INVENTION

The present invention provides an apparatus for automatically measuring fluid flow through a channel and collecting samples from the channel on the basis of time or flow rate. The apparatus includes a fluid sampling assembly, a flow measuring assembly and a computer control means integrally incorporated within a unitary case. The sampling assembly has an inlet selectively connected to a sample intake conduit which is adapted to extend to the fluid in the channel. The flow measuring assembly has a sensing means selectively connected thereto for detecting a variable related to the fluid flow rate in the channel and outputting a signal proportional thereto. The flow measuring assembly includes means for processing signals from the sensing means for input to the computer control means. The computer control means is programmed to calculate the flow rate in the channel on the basis of processed signals from the flow measuring assembly, automatically control sampling operation of the sampling assembly in proportion to time or the calculated flow rate, and automatically collect and store data relating to operation of the apparatus.

The apparatus according to the invention may selectively be used only for collecting samples, only for monitoring flow rate, or for simultaneously collecting samples and monitoring flow rate, as desired.

In one preferred embodiment, a flow restricting device is disposed in an open flowing channel and the sensing means of the flow measuring assembly is operably disposed relative thereto. The sample intake conduit of the sampling assembly is disposed on the discharge side of the flow restricting device. The data stored by the computer control means includes data relating to operation of the sampling assembly and flow rate data. The data may be viewed by the user on display means provided on the case, or may be transferred via a portable external data transfer unit to a remote output device such as a computer and/or printer.

The invention also provides a method for automatically measuring fluid flow through a channel and collecting samples from the channel on the basis of time or flow rate. The method comprises the steps of: connecting a sensing means to a flow measuring assembly for detecting a variable related to the fluid flow rate in the channel; connecting a sample intake conduit to an inlet of a sampling assembly; mounting the sensing means in a detecting position relative to the channel; lowering an intake end of the conduit into the fluid in the channel; and suspending an integral operating unit, including the fluid sampling assembly, the fluid flow measuring assembly and a computer control means, in a sewer manhole. The method further comprises the step of operating the computer control means to calculate the flow rate in the channel on the basis of signals received from the flow measuring assembly, automatically control sampling operation of the sampling assembly in proportion to time or the calculated flow rate, and automatically collect and store flow rate data and data relating to operation of the sampling assembly.

It is an object of the present invention to provide an integral and compact unitary structure embodying both a fluid sampling assembly and a fluid flow measuring assembly together with computer control means for automatically operating same. The case in which the components are housed is conveniently mountable in a sewer manhole, and the fluid intake conduit and sensor leading from the same case can be conveniently positioned relative to a channel.

A further object of the invention resides in the storage of flow rate data at user-selected intervals, and the storage of data relating to operation of the sampling assembly, such as times and dates of collected and/or missed samples and parameters of the sampling program such as the volume of the collected sample, the interval between samples, and time or flow units remaining until the next sample.

A related object of the invention is to permit display of stored flow rate and/or sampling data on a display mounted on the case of the apparatus, or transfer of the stored data to a remote output device. Transfer of stored data is accomplished by means of a portable pocket-sized data transfer unit which is connected via an external connector on the case of the apparatus with the computer control means of the apparatus to retrieve stored data as desired. The data transfer unit can be conveniently transported and connected to any desired remote output device, such as a computer and/or printer, to permit transfer of the stored data to such output device. Transfer of stored data may also be accomplished by direct connection of the apparatus of the invention to a computer or terminal.

The above and further objects, details and advantages of the invention will become apparent from the following detailed description, when read in conjunction with the accompanying drawings.

DETAILED DESCRIPTION OF THE PREFERRED EMBODIMENTS

FIGS. 1-3, 4A and 4B depict an automatic fluid sampling and flow measuring apparatus according to a first embodiment of the invention.

Figure 1:
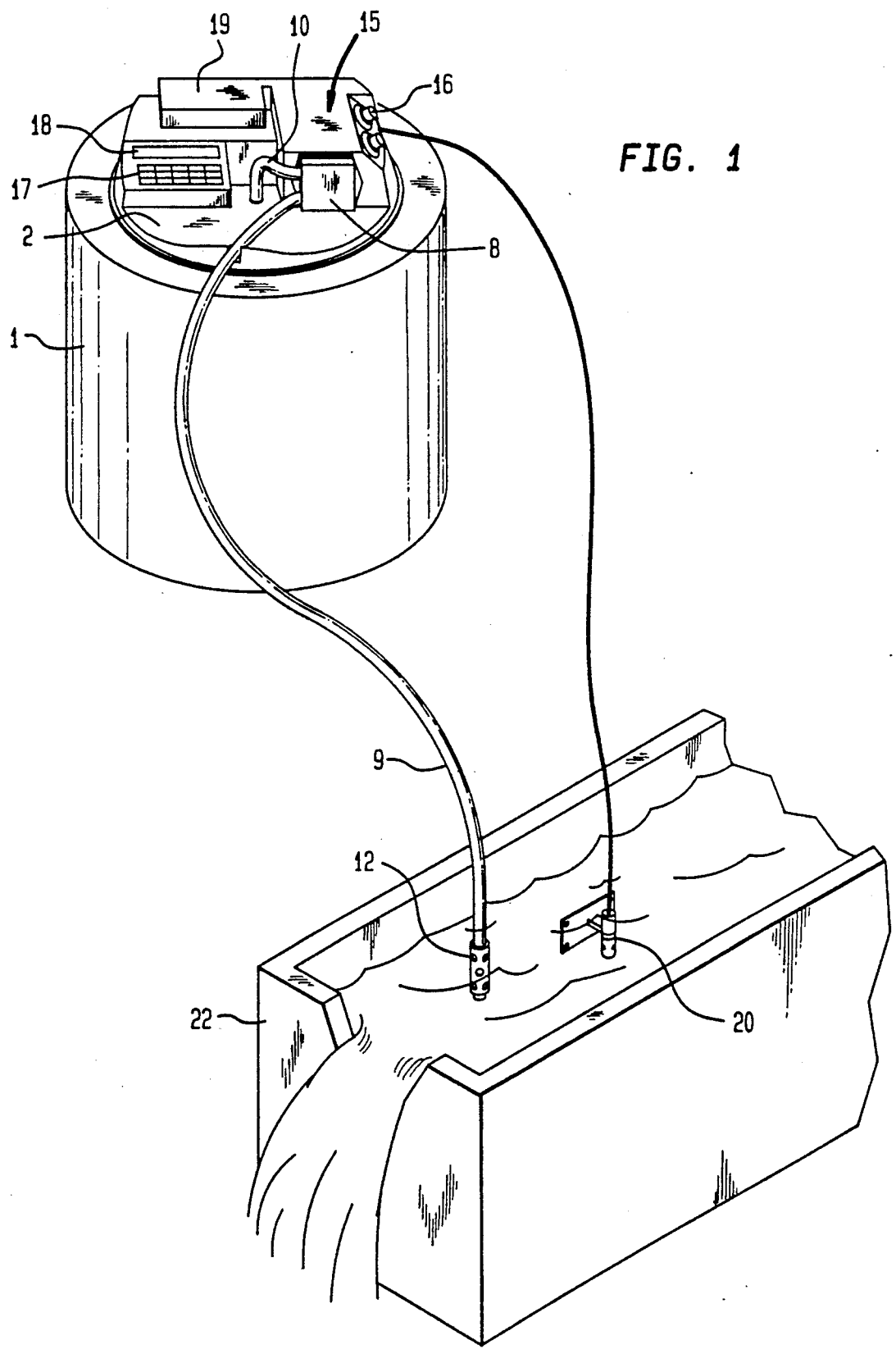
FIG. 1 is a perspective view of a sampling and flow rate measuring apparatus according to a first embodiment of the invention, having a fluid intake conduit and a sensing means connected thereto and mounted in operative position relative to a channel.
Figure 2:
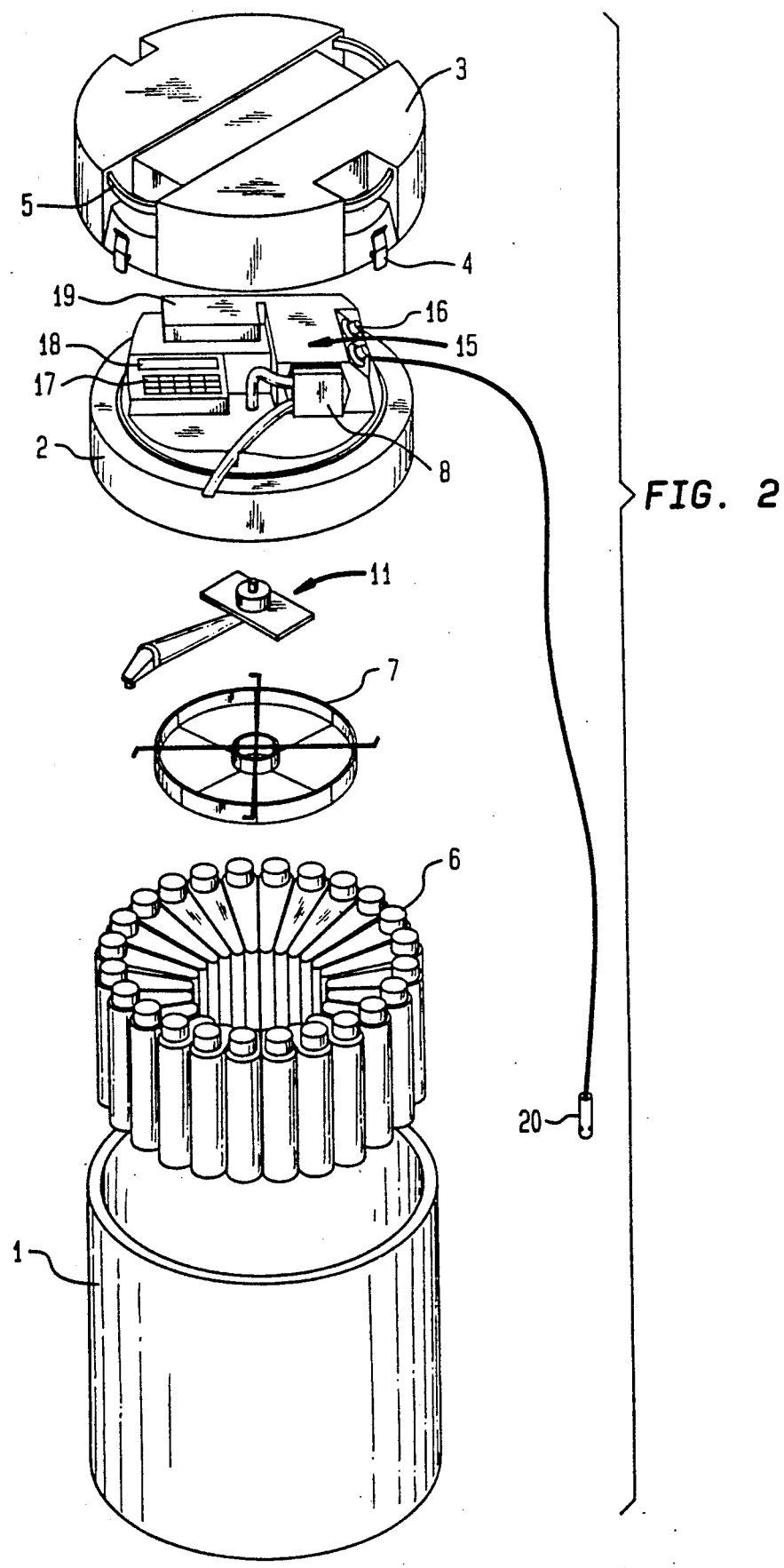
FIG. 2 is a disassembled view of the apparatus according to the first embodiment of the invention, showing the interrelationship of various components thereof.

As shown in FIGS. 1 and 2, the apparatus includes a case comprising a lower portion 1 for holding one or more sample containers, an upper component supporting portion 2 and a top cover 3. Each portion of the case is preferably fabricated of a rugged thermoplastic material, such as molded polyethylene, which is impact resistant and capable of withstanding the stresses of mounting and use in a sewer manhole. The upper component-supporting case portion 2 is adapted to be tightly received in the upper end of lower case portion 1, and the top cover 3 is removably received over upper case portion 2 to protectively enclose the components supported by case portion 2, and to close the case. Top cover 3 is provided with a plurality of fasteners 4 adapted to mate with fastening portions provided at the upper outer surface of lower case portion 1, and handles 5 for ease of transport of the apparatus.

The lower case portion 1 is shown in FIG. 1 as accommodating therein a plurality of sample containers 6. Lower case portion 1 is preferably double-walled with approximately 1" of insulation, for example, to insulate the interior thereof for storing ice to keep sample containers cool. The sample containers 6 are shown in the form of 24 one-liter bottles made of polyethylene or glass, for example. It is to be understood, however, that any number of sample containers ranging from only one to a multiplicity thereof may be employed. Sample containers 6 are supported in a generally circular array.

Figure 7:
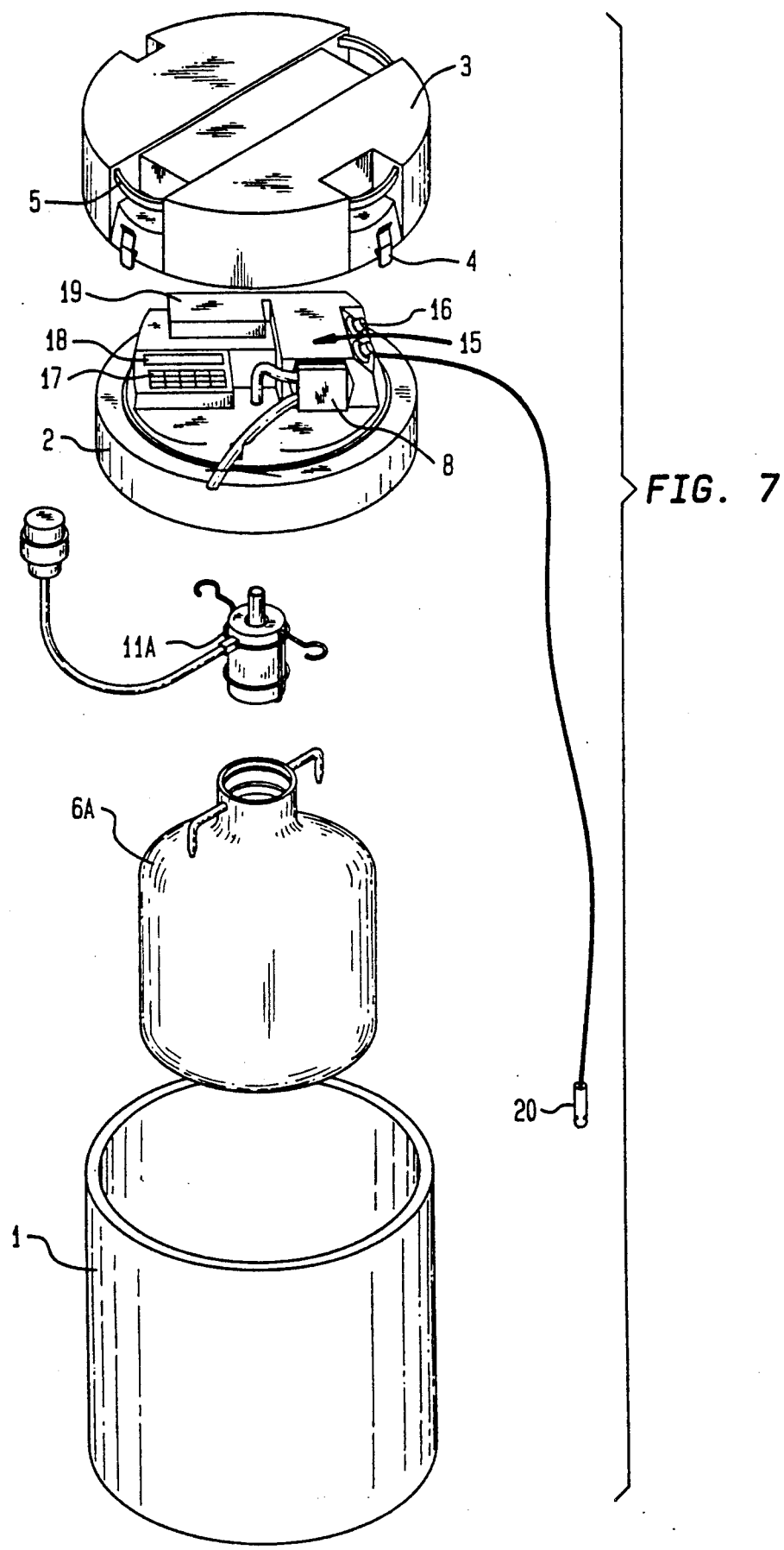
FIG. 7 is a view, similar to FIG. 2, showing another embodiment wherein a single sampler container is provided in the lower case portion.

In the alternate embodiment shown in FIG. 7, a single large sample container 6A is accommodated in lower case portion 1 rather than the plurality of containers 6 shown in FIG. 2.

The fluid sampling assembly of the invention may take any desired form of fluid sampler capable of automatic control by a microprocessor to take repeated accurate samples. A sampler having desired characteristics is described in the aforesaid U.S. Pat. No. 4,660,607 issued in 1987 to Griffith et al, the disclosure of which is incorporated herein by reference thereto.

The fluid sampling assembly employed in preferred embodiments of the present invention is substantially similar to that disclosed in U.S. Pat. No. 4,660,607, and thus only a general description thereof is set forth herein. The assembly includes a reversible, positive displacement pump 8 mounted in casing portion 2 and having the inlet thereof selectively connected to a suitable length of sample intake conduit 9. Provided at the lower intake end of conduit 9 is a weighted strainer member 12 which holds the end of the conduit under water and prevents larger objects from entering and blocking the conduit. A second length of conduit 10 is connected between the outlet of pump 8 and an electromechanical distributor mechanism 11 for routing fluid samples to any of the containers 6. A positioning insert 7 is provided between the distributor mechanism 11 and tray 6A. For the single sample container 6A embodiment shown in FIG. 7, the positioning insert 7 and distributor mechanism 11 are replaced by a sample directing member 11A.

The pump 8 is cyclically operated in a reverse purging direction or a forward sample drawing direction depending on signals supplied by processing means incorporated in the computer control means of the present invention, which will be described in detail below. The processing means determines the rate of liquid flow and the time the pump must operate to fill all the tubing plus a desired sample volume, on the basis of samples from a fluid detection sensor disposed upstream of the pump 8, and user programmed data relating to the tubing 9.

As shown in FIGS. 1 and 2, case portion 2 supports other components of the invention in addition to sampler pump 8. The computer control means 15 of the invention is supported by case portion 2, together with a number of external connectors 16 which provide access to computer control means 15. Also supported by case portion 2 is a user-input keypad 17, an alphanumeric display 18 and power supply means 19 which may take the form of a rechargeable battery and/or a power pack for alternatively supplying power to the apparatus from an external AC power source. The aforesaid components supported by case portion 2 are mounted in a watertight manner to protect same from adverse external conditions. Additional protection of such components is afforded by fastening top cover 3 in position, although even without top cover 3 the case with the components mounted therein is submersible, watertight, dust-tight, corrosion resistant and ice resistant (e.g., NEMA 4x, 6).

The fluid flow measuring assembly of the invention, described in detail below, has selectively connected thereto via one of the external connectors 16 a sensor 20 for detecting a variable related to the fluid flow rate in a channel. In the embodiment of FIGS. 1-4, the sensor takes the form of a pressure transducer adapted to be submerged in the fluid of a channel to convert ambient pressure to an electrical voltage signal. The voltage output from sensor 20 is proportional to the distance below the liquid surface at which sensor 20 is disposed. A suitable mounting bracket is provided for fixing sensor 20 in a submerged position.

In accordance with one preferred embodiment of the invention, a fluid flow restricting device 22 as shown in FIG. 1 may be installed in an open flowing sewer passage to define a fluid channel for measuring fluid flow rate. Alternatively, the fluid channel may be defined by the open flowing sewer passage itself. Where as here a restricting device 22 is employed, samples are typically collected on the discharge side of the device.

Although the device 22 shown in FIG. 1 takes the form of a V-notch weir, it will be understood that other suitable flow restricting devices may alternatively be employed. For example, device 22 may comprise a flume (e.g., H-flume, Parshall flume, trapezoidal flume, Palmer-Bowlus flume or Leopold-Lagco flume), another type of weir (e.g., rectangular weir with or without end contractions, or Cipolletti weir), or a nozzle (e.g., Kennison or parabolic nozzle).

Each of the foregoing devices, like the V-notch weir 22, is adapted to restrict fluid flow in an open passage so as to increase the liquid depth upstream of the device. The upstream liquid depth or "head" of each such device has a known mathematical relationship with the rate of flow through the channel of the device. This head vs. flow rate relationship is available in published form for various different sizes of each type of device (e.g., see *Stevens Water Resources Data Book*, Leupold & Stevens, Inc., 1978). Where the flow rate is measured directly from an opening flowing sewer channel, the necessary flow rate relationship is determined on the basis of the dimension, declination, and inside roughless of the pipe.

When the sensor 20 is submerged upstream of the above-described flow restriction as shown in FIG. 1, the voltage output from sensor 20 will be directly related to the "head" value used to calculate the flow rate. Typically, the sensor 20 will be mounted at a low point in the flow restriction device 22 so that it will remain submerged. Processing of the signals from sensor 20 and calculation of the flow rate is performed by the fluid flow measuring assembly and the computer control means of the invention as described below.

The computer control means and fluid flow measuring assembly according to the first embodiment of the invention will be described in detail with reference to FIGS. 3 and 4A-4B. The boxes labelled "A/D Converter" and "Signal Conditioning Electronics" shown to the right of the dashed line in FIG. 3 essentially comprise the fluid flow measuring assembly according to the invention, to which the sensor 20 is selectively connected. The A/D converter and signal conditioning electronics together define interface means through which a precision voltage level is supplied to the sensor, and signals detected from the sensor are conditioned and converted to a digital form for input to the computer control means.

More specifically, the interface means includes electronic circuitry, with amplifiers and an analog to digital converter, provided on a single board which is integrally connected with the computer control means. The interface means functions to provide a precision voltage level to the sensor 20, and to detect signals from the sensor 20. The detected signals are amplified and smoothed (filtered for noise), and then converted to digital form by the A/D converter for input to the computer control means.

The computer control means according to the invention preferably comprises a microprocessor having pre-installed firmware in read-only memory, such as programmed EPROM chips. In addition to the program storage memory, the microprocessor is provided with data storage memory in the form of random access memory (RAM) which stores specific details of operation set by the user and records flow and sampling data as described in detail below. The data storage memory (RAM) is backed-up by its own battery, e.g., a lithium battery, so that data will remain stored therein even when the overall power source of the apparatus is turned off. The stored data will thus remain available under a new sampling cycle is started.

The program storage memory of the microprocessor includes the following programming, each of which will be described in detail:
  Interface Programming;
  Sampling Assembly Programming; and
  Flow Measuring Assembly Programming.

The Interface Programming allows the microprocessor to control the user input keypad 17, alphanumeric display 18, and a real-time clock (FIG. 3); and to access the active interface devices including the sampler pump 8, the distributor mechanism 11 and the sensor 20. As described above, the interface and signal conditioning electronics of the flow measuring assembly are shown to the right of the dashed line in FIG. 3. Interface and signal conditioning electronics are also provided for the sampling assembly.

The Sampling Assembly Programming allows the microprocessor to control the sampling assembly by implementing user-programmed parameters stored in the data storage memory. The sampling assembly programming includes algorithms using real time, elapsed time and flow rate to collect liquid samples using the sampling assembly and the distributor mechanism. Operation of this programming is controlled by user-programmed parameters, described below with reference to the data storage memory.

The Flow Measuring Assembly Programming allows the microprocessor to calculate the fluid depth and flow rate on the basis of processed signals received from the flow measuring assembly. The programming includes depth vs. flow equations which characterize the relationship between the "head" and flow rate for various types and sizes of fluid flow restricting devices. Floating point math algorithms are provided to enable the microprocessor to perform high precision mathematical operations required to accurately calculate the values of a fluid flow-related variable. Such fluid flow-related variable comprises fluid depth which is calculated from the output of the submerged sensor 20, and to calculate the flow rate from the measured fluid depth. Algorithms are included for performing addition, subtraction, multiplication, division, exponentiation, logarithms and trigonometry functions to a precision equivalent to over four significant figures.

Having described the various types of programming provided in the program storage memory (EPROM) of the microprocessor, functioning of the data storage memory (RAM) of the microprocessor will now be described with reference to FIGS. 3 and 4A-4B. The data storage memory (RAM) is used for storing specific details of operation set by the user, and recording flow and sampling data.

The sampling program parameters to be input by the user via keypad 17 and stored in RAM include: program start and stop criteria, time and/or flow interval between samples, size of the sample, container for sample storage and rinse and fault conditions for intake conduit 9. These parameters are set out in the leftmost "User Command" column in FIG. 4A, under "Specify Sampler Program". The invention contemplates that the microprocessor be programmed to sequentially prompt the user (via display 18) to enter these and other desired parameters via keypad 17.

The microprocessor is programmed such that data will be collected during execution of a liquid sampling program, and will be stored in RAM. Such data includes all programmed entries, the time and date for each collected sample, data relating to any failed attempts to collect liquid samples, volume collected, volume remaining, bottle number, and time remaining until the next sample.

The fluid flow-related parameters to be input by the user via keypad 17 and stored in RAM include: the type and size of the flow restricting device being used, calibration data for the submerged pressure transducer/sensor 20, the desired flow rate units, the desired interval for sample collection, and the desired interval for recording flow data. The flow-related parameters are set out in the columns marked "Specify Flowmeter Operation" and "Calibrate Submerged Pressure Transducer" in the User Command section of FIG. 4A.

Flow rate data will be stored in RAM in accordance with the parameters thus set by the user. As shown in the lowermost box of FIG. 4B, the flow rate data is to be stored may include the time, date and value for flow rate at a user-selected interval; a daily value for minimum, maximum and average flow rate; daily cumulative flow; overall average flow rate and cumulative flow; local flow minimums and maximums, etc.

Figures 4, 4A:
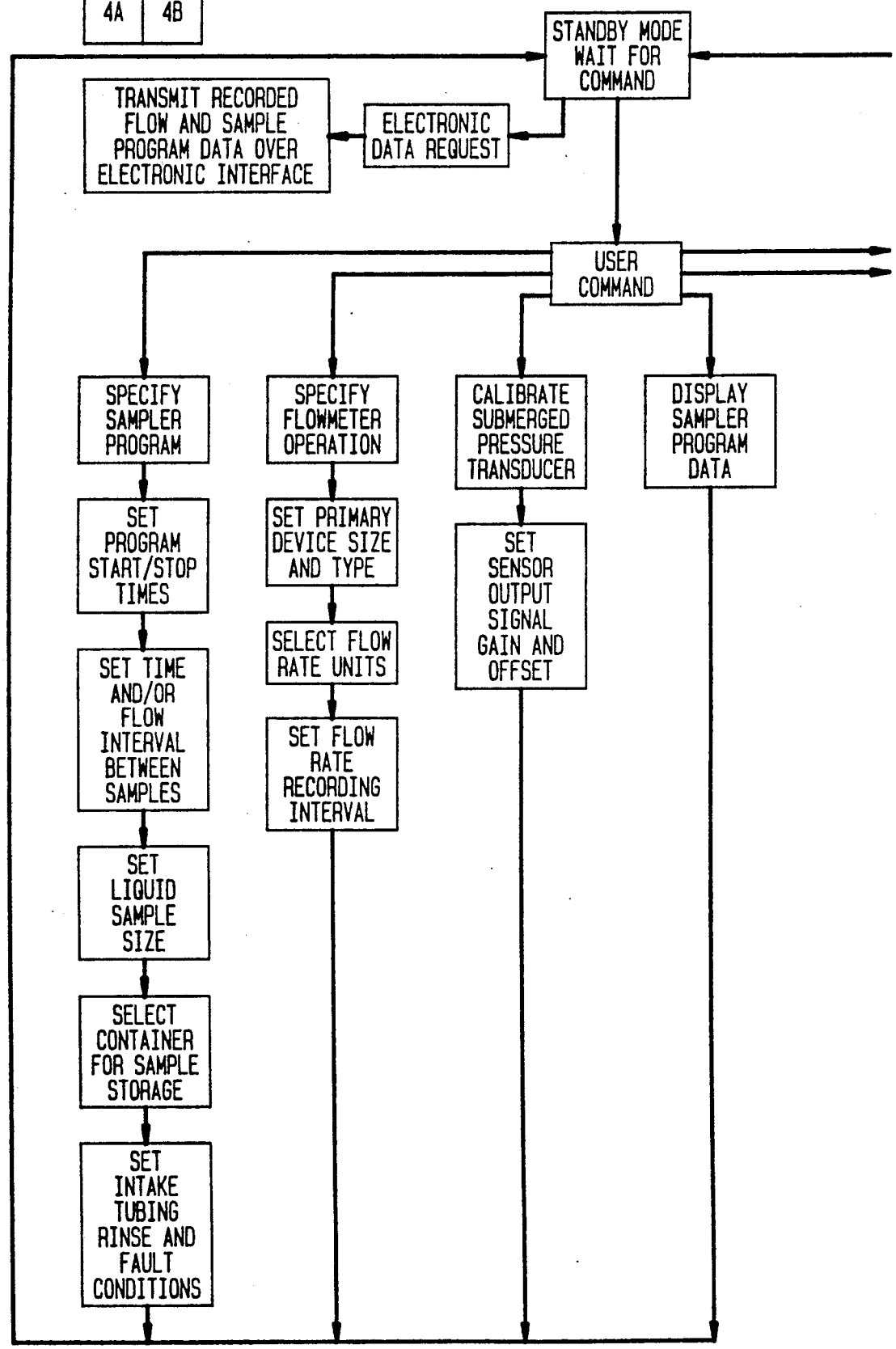
FIGS. 4, 4A and 4B together define a flow chart showing operational sequences of the apparatus according to various user commands.
Figure 4B:
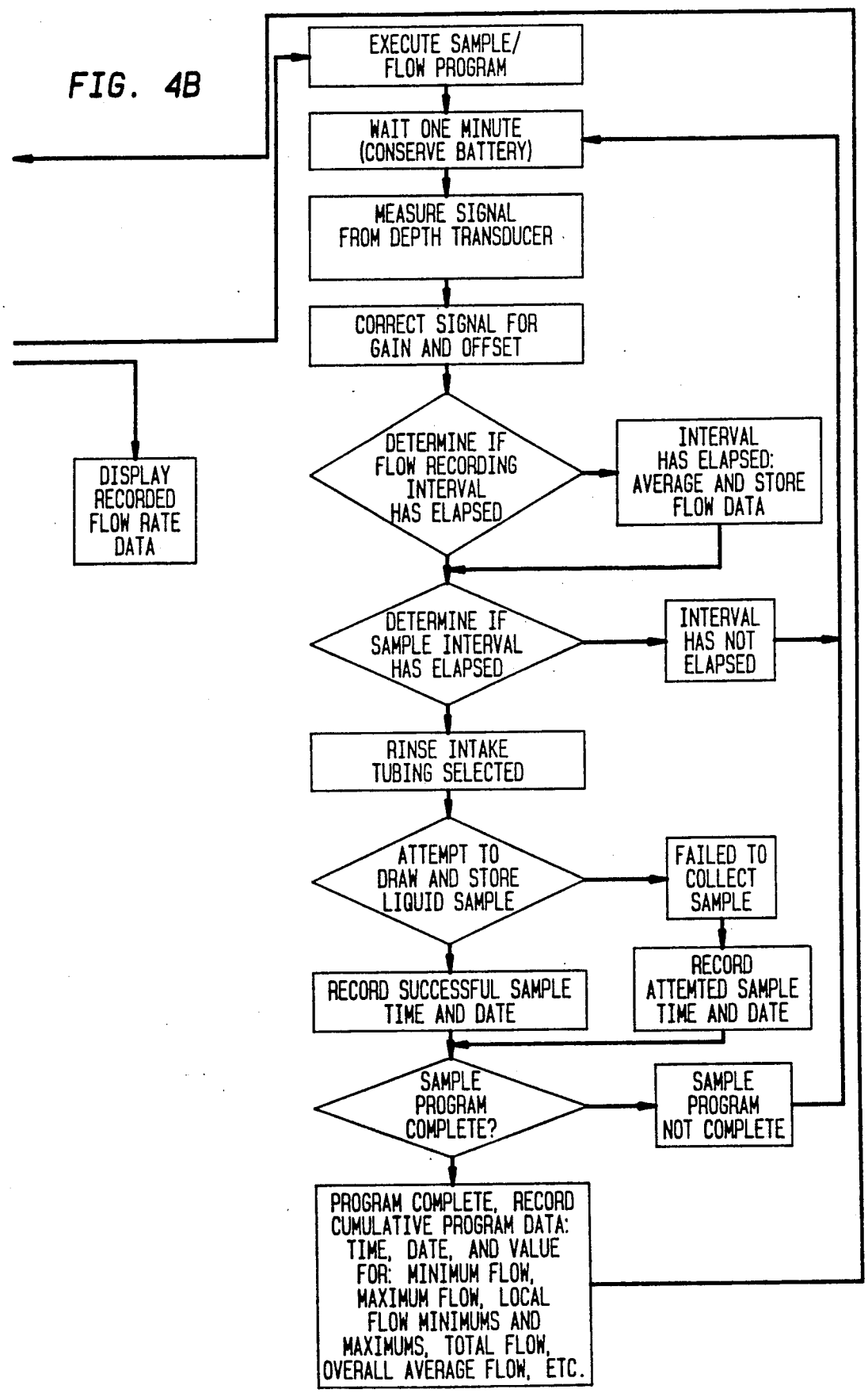

As also depicted in the User Command section of FIGS. 4A-4B, the user can request (via keypad 17) that the sampler program and flow rate data stored in RAM be displayed on display 18 when desired. As noted above, the data storage memory of the invention comprises battery backed-up RAM, so that stored data will remain available for retrieval by the user until a "start" button is pressed to begin a new sampling cycle.

Figure 3:
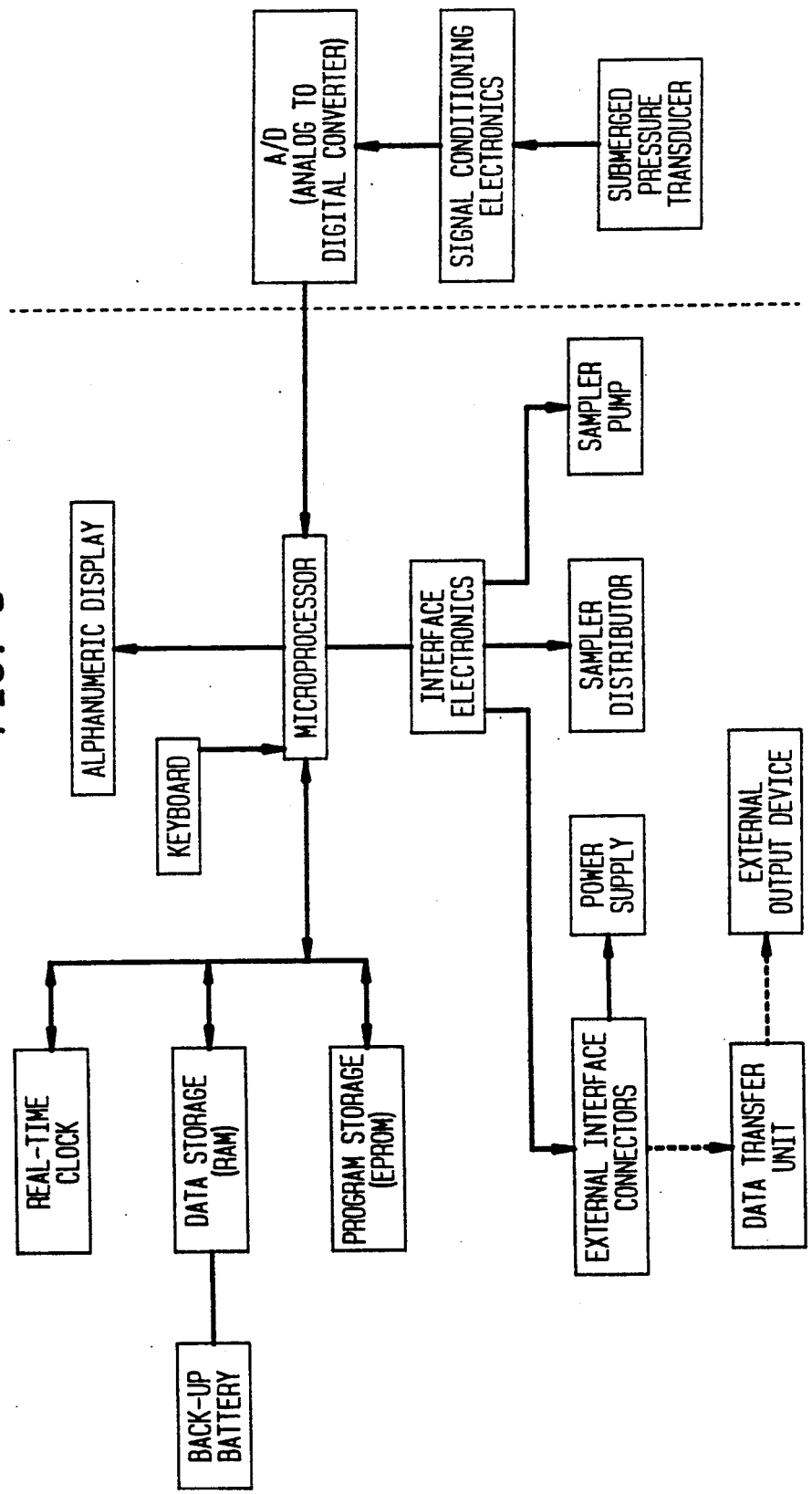
FIG. 3 is a block diagram of the various components of the first embodiment of the invention as controlled by the computer control means.

The invention provides an alternative means for retrieving stored sampler program and flow rate data in the form of a portable data transfer unit, indicated in the lowermost box of FIG. 3. The portable data transfer unit is preferably very compact, i.e., pocket-sized, so that the user can conveniently carry same for selective use. The data transfer unit is provided with its own microprocessor, the memory of which may take the form of CMOS RAM chips powered by a lithium battery (battery backed-up RAM). The unit is also preferably provided with a user-input keypad and an alphanumeric display, and would resemble a conventional small pocket calculator in overall appearance.

The data transfer unit is connected via a conventional connector cable (not shown) with one of the connectors 16, which may comprise a conventional 6-pin computer connector jack but which provides for a watertight connection. The user may then send an electronic data request command from the data transfer unit to the microprocessor of the sampling and flow measuring apparatus, as indicated diagrammatically in the upper left portion of FIG. 4A. Upon receipt of such command, the microprocessor of the overall apparatus retrieves the requested data from its RAM and sends it for storage in the memory of the data transfer unit, via the connector 16.

When it is desired to retrieve the data thus stored in the data transfer unit, the unit is in turn connected, via a computer or printer jack for example, to an external output device (FIG. 3). It is to be understood that the external output device depicted diagrammatically in FIG. 3 may take the form of a conventional printer or computer (e.g., personal computer). The stored data can be read out directly on a line printer to produce a hard copy thereof, with the microprocessor of the data transfer unit itself operating the printer in a known manner. The user is thus able to obtain a complete and accurate hard copy record of the data. Alternatively, the stored data can be transferred to a conventional computer for manipulation using an available software program for statistical analyses, spreadsheeting, etc.; for more permanent storage in a database stored in the computer's memory; and/or for printing by a printer connected to the computer.

It is to be understood that the novel data storage and transfer means in accordance with the invention is not restricted to use with the fluid sampling and flow measuring apparatus of the invention, and can be readily adapted for use with either a sampler or a flow meter functioning as independent units. Further, when used in conjunction with the fluid sampling and flow measuring apparatus of the invention, the data transfer means can be used to selectively transfer sampling data only, flow rate data only, or both types of data, as desired.

The data transfer means according to the invention can also be used in conjunction with a stationary refrigerated sampling and flow measuring apparatus, such as might be installed in a waste treatment plant. In this connection, it is to be understood that the fluid sampling and flow measuring apparatus according to the invention can be adapted to such an installation by adding electric refrigeration means thereto.

Although it may not often be practical, the external connector 16 described above can alternatively be directly linked to a remote computer for direct transfer of the stored data if and when the apparatus itself is transported into close proximity with a computer. However, use of the portable data transfer unit offers a more convenient means for transferring the data.

Figure 5:
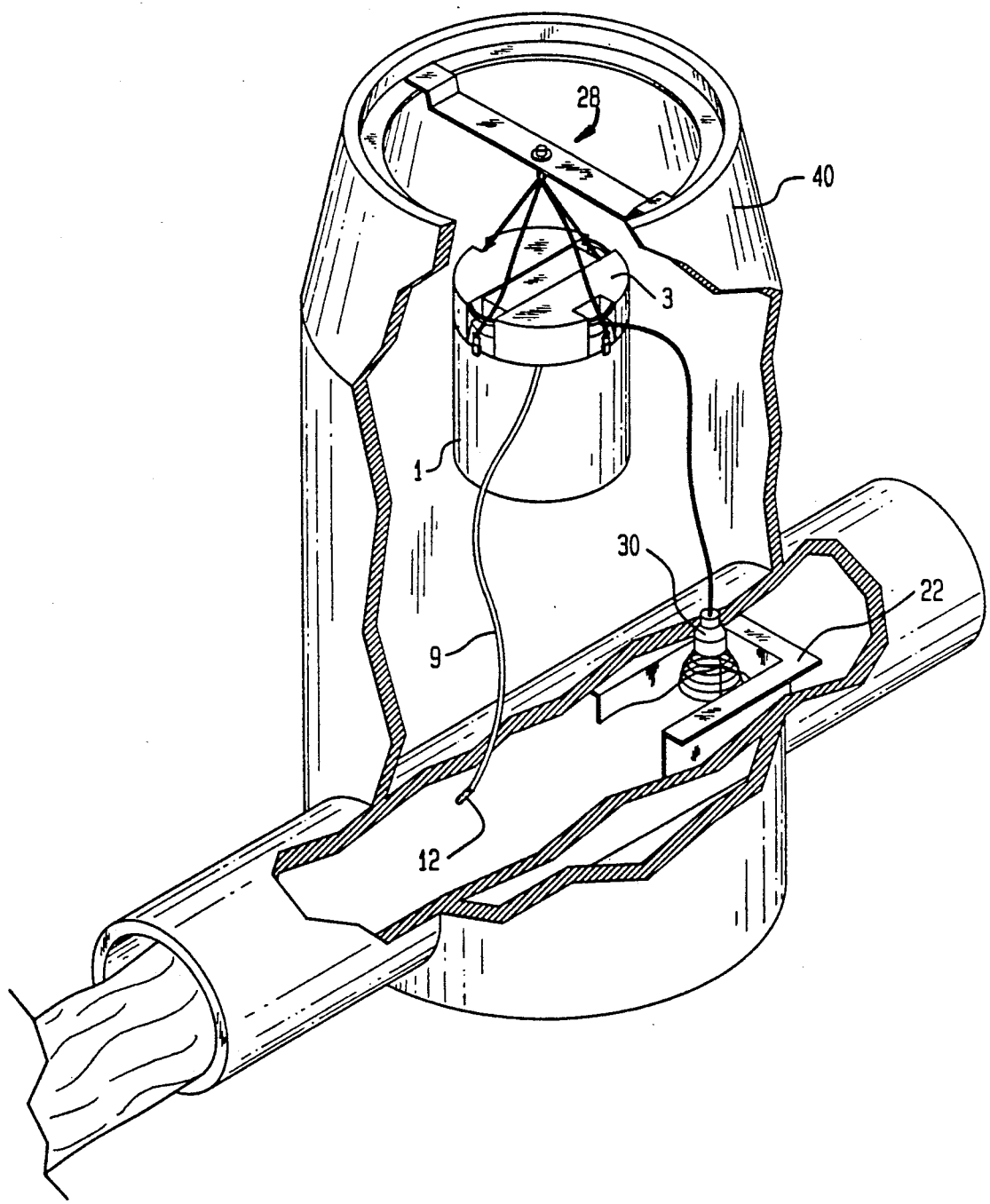
FIG. 5 is a perspective view of a sampling and flow rate measuring apparatus according to a second embodiment of the invention, including an ultrasonic sensing means, and shown as mounted in a sewer manhole.
Figure 6:
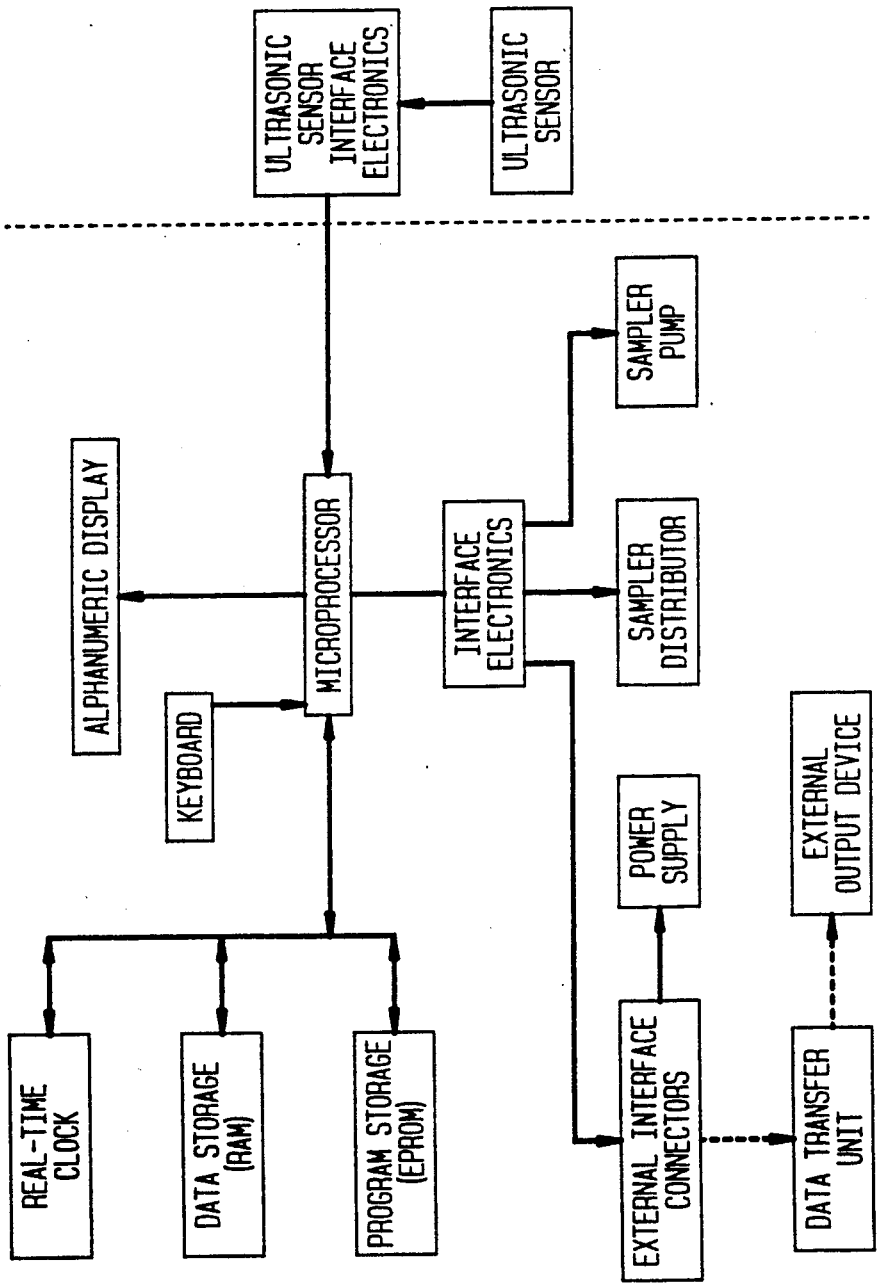
FIG. 6 is a block diagram of the various components of the second embodiment of the invention as controlled by the computer control means.

Turning now to the second embodiment of the invention shown in FIGS. 5 and 6, here the sensing means comprises an ultrasonic echo range sensor 30 rather than the pressure transducer sensor 20 of the first embodiment. With the exception of the fluid measuring assembly, including the interface electronics and the sensor, the apparatus of the second embodiment remains substantially the same as that of the first embodiment.

In FIG. 5, the apparatus is shown in a mounted position within a sewer manhole. A suspending means 28 includes a cross-bar support extending across the upper end of the manhole and a plurality of lines extending from the support to fastening portions provided on the case of the apparatus. If desired, such fastening portions may comprise portions of fasteners 4 used to fasten cover 3 to lower case portion 1.

In this embodiment, the ultrasonic sensor 30 is mounted in position above the fluid in the flow restricting device 22. Any suitable mounting means may be used for mounting sensor 30, provided that the sensor 30 is held in position above the fluid and out of contact therewith. The ultrasonic sensor 30 uses an echo range measurement through air technique to measure the distance from a fixed point above the channel to the fluid surface. The output from sensor 30 based on such measurement can then be used by programming provided in the microprocessor to calculate the depth of the fluid in the channel and the rate of flow.

As shown to the right of the dashed line in FIG. 6, the flow measuring assembly in the second embodiment comprises interface means in the form of ultrasonic sensor interface electronics for sensor 30. As in the first embodiment, the interface electronics for sensor 30 can be provided on a single board which is integrally connected with the microprocessor. Here the interface means cooperates with sensor 30 such that short pulses from a high-energy, high-frequency source are amplified and directed toward the fluid surface by sensor 30, and weak echo signals are reflected back and amplified. Timing circuitry in the interface means clocks the amount of time for the echo signals to return. This value is then input to the computer control means for calculating the flow rate therefrom.

It will be understood that the only differences between the first and second embodiment reside in the type of depth sensor used and the interface electronics therefor. In this respect, a skilled technician could convert the fluid measuring assembly of the apparatus from one type to the other by replacing the circuit board containing the sensor interface electronics and thereby adapting the apparatus for use with the other type of sensor.

It will also be understood that the invention is not limited to the two types of sensors described, and other suitable known flow rate sensing means may alternatively be employed, including both means for measuring head in an open channel arrangement with a flow restricting device and any other means for measuring flow without employing a flow restricting device.

Figure 8:
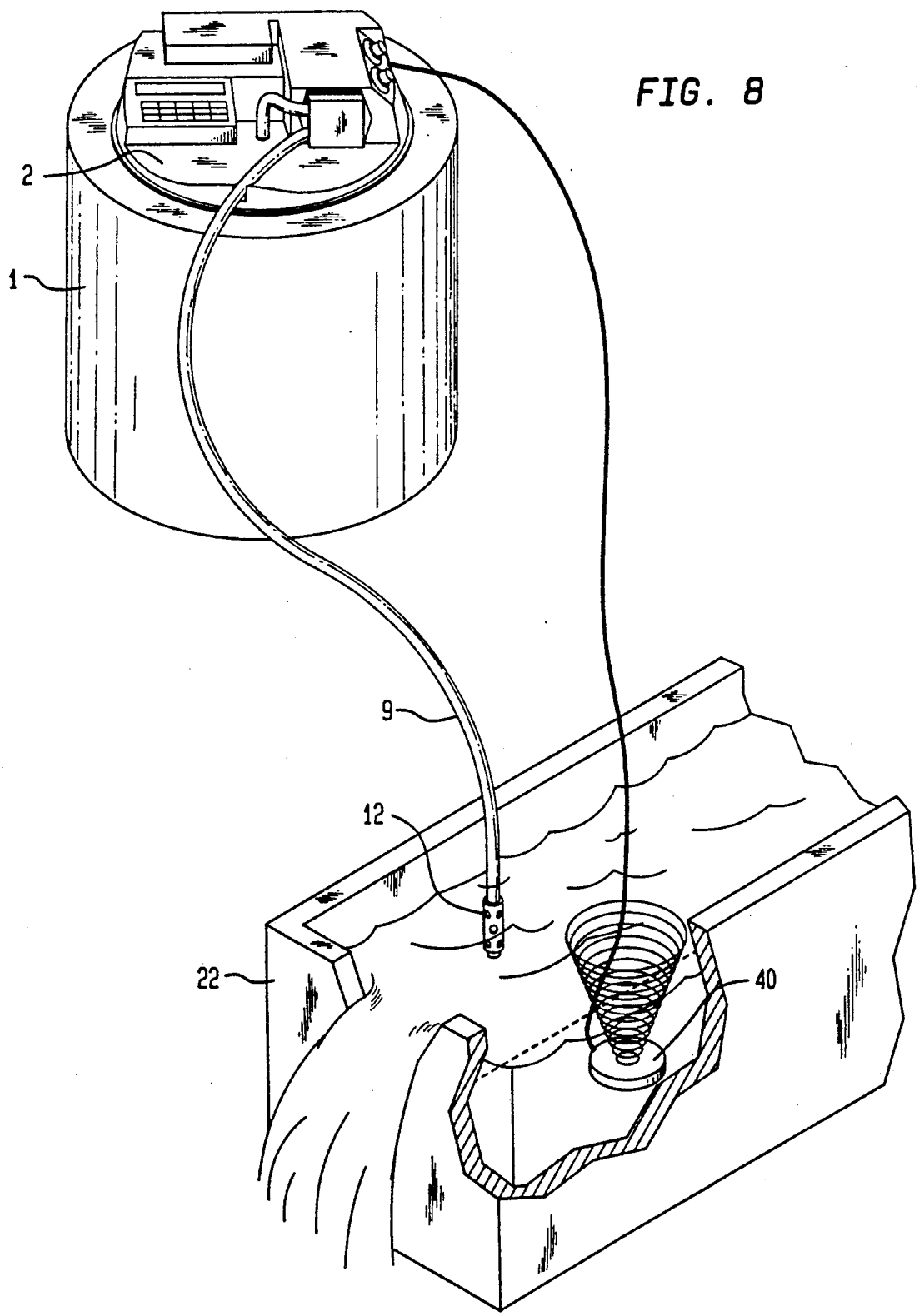
FIG. 8 is a perspective view of the apparatus including another type of ultrasonic sensing means.

In FIG. 8, the sensing means comprises an ultrasonic sensor 40 using an echo range measurement through liquid technique to measure the distance from the bottom of the channel to the fluid surface. The fluid depth is thus measured by timing the sound reflections from the surface of the fluid in the channel. Suitable interface means are provided for sensor 40, similar to those described with reference to sensor 30.

Figure 9:
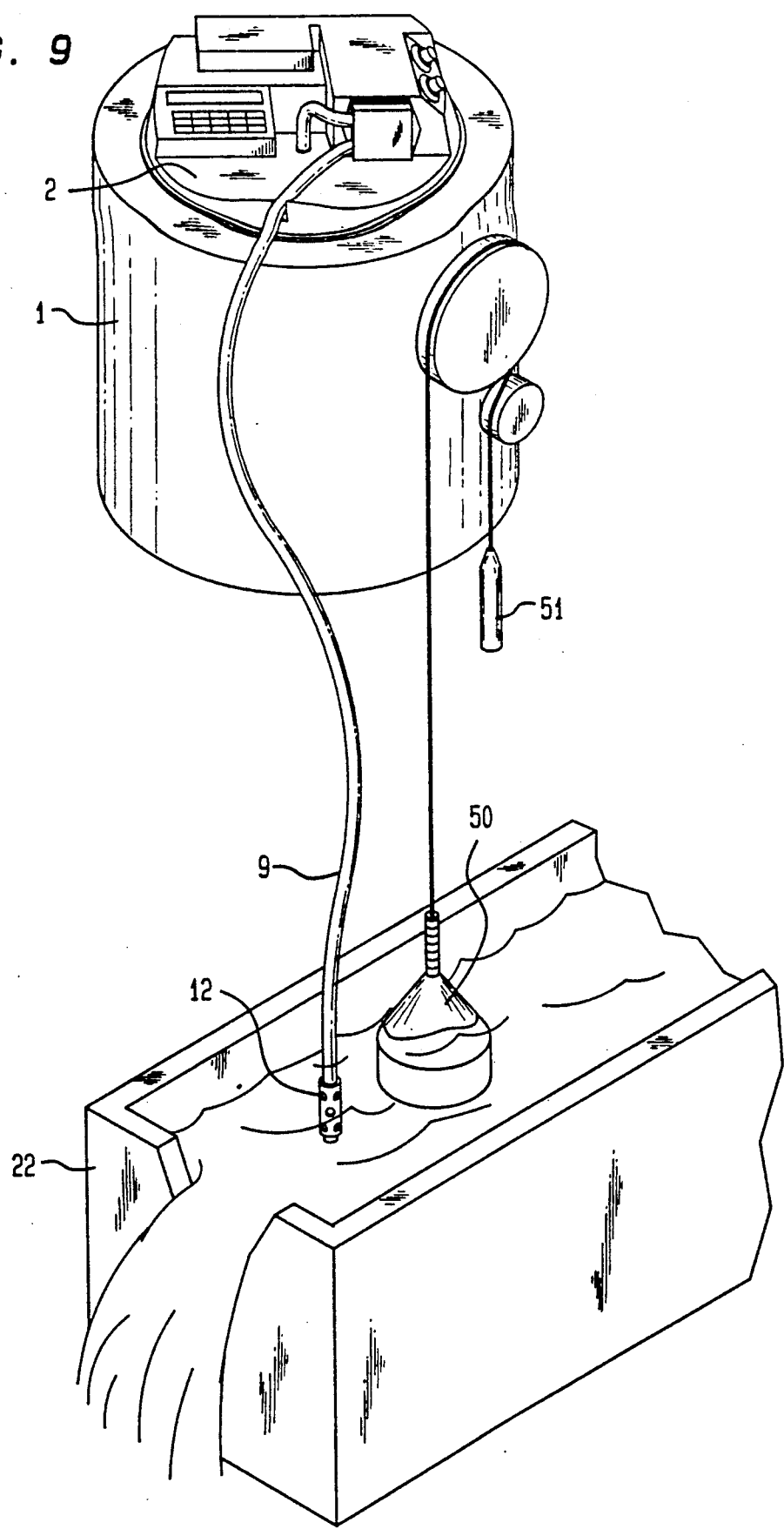
FIG. 9 is a perspective view of the apparatus including a float-type sensing means.

A float type sensor 50 such as shown in FIG. 9 may also be used for the sensing means of the invention. The fluid depth in the channel is indicated by the position of the float 50, with a counterweight 51 being provided to improve accuracy by offsetting part of the weight of float 50. Suitable interface electronics for the float type sensor 50 are connected with the microprocessor of the apparatus.

Figure 10:
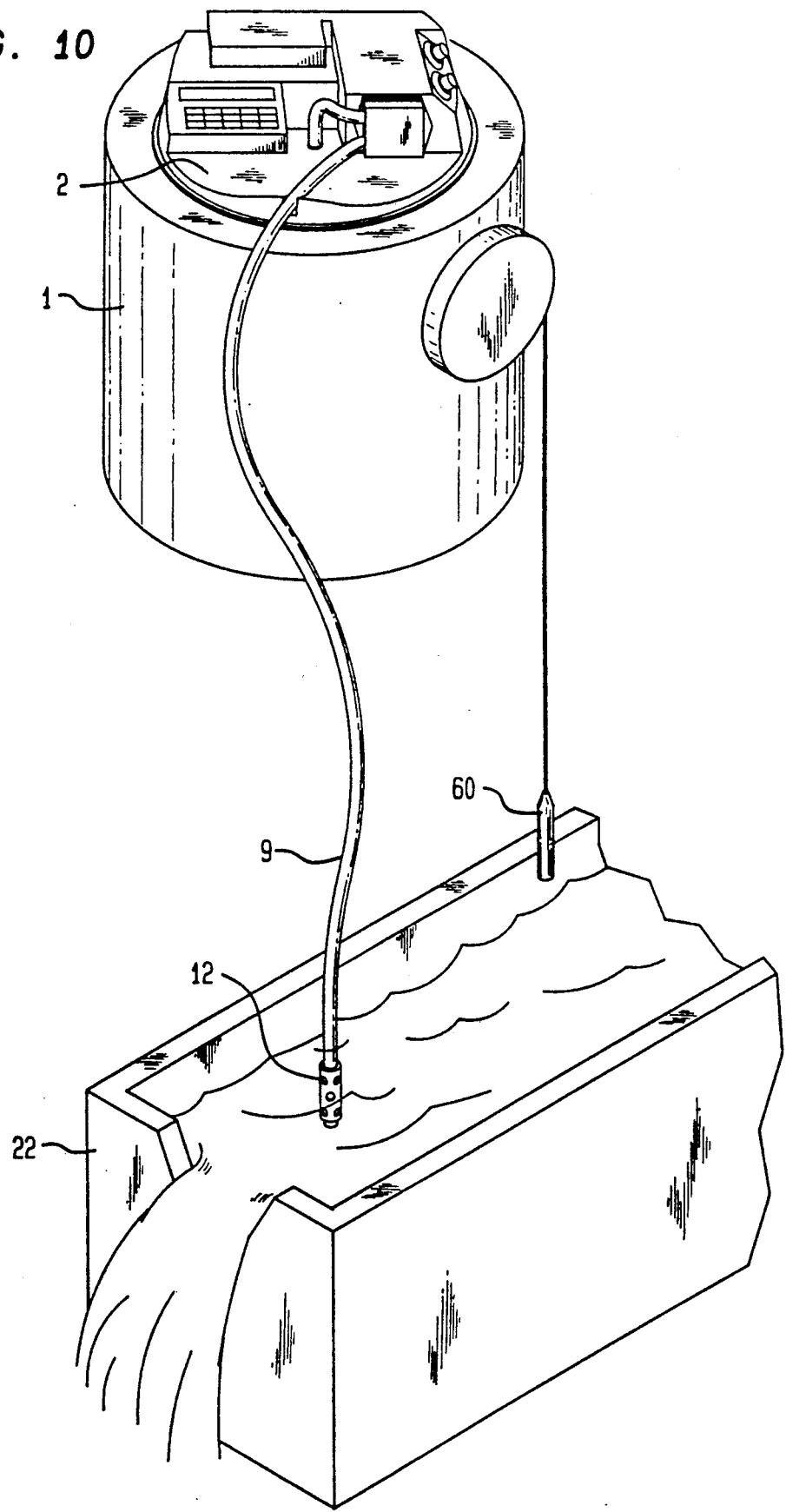
FIG. 10 is a perspective view of the apparatus including a dipper-type sensing means.

FIG. 10 depicts a dipper type sensor 60 which may alternatively be employed as the sensing means of the invention. The sensor 60, operating on a conductivity principle for example, is repeatedly raised and lowered to locate the surface of the fluid in the channel, from which the depth of fluid in the channel can be calculated. Suitable interface electronics for the dipper type sensor 60 are connected with the microprocessor of the apparatus.

Figure 11:
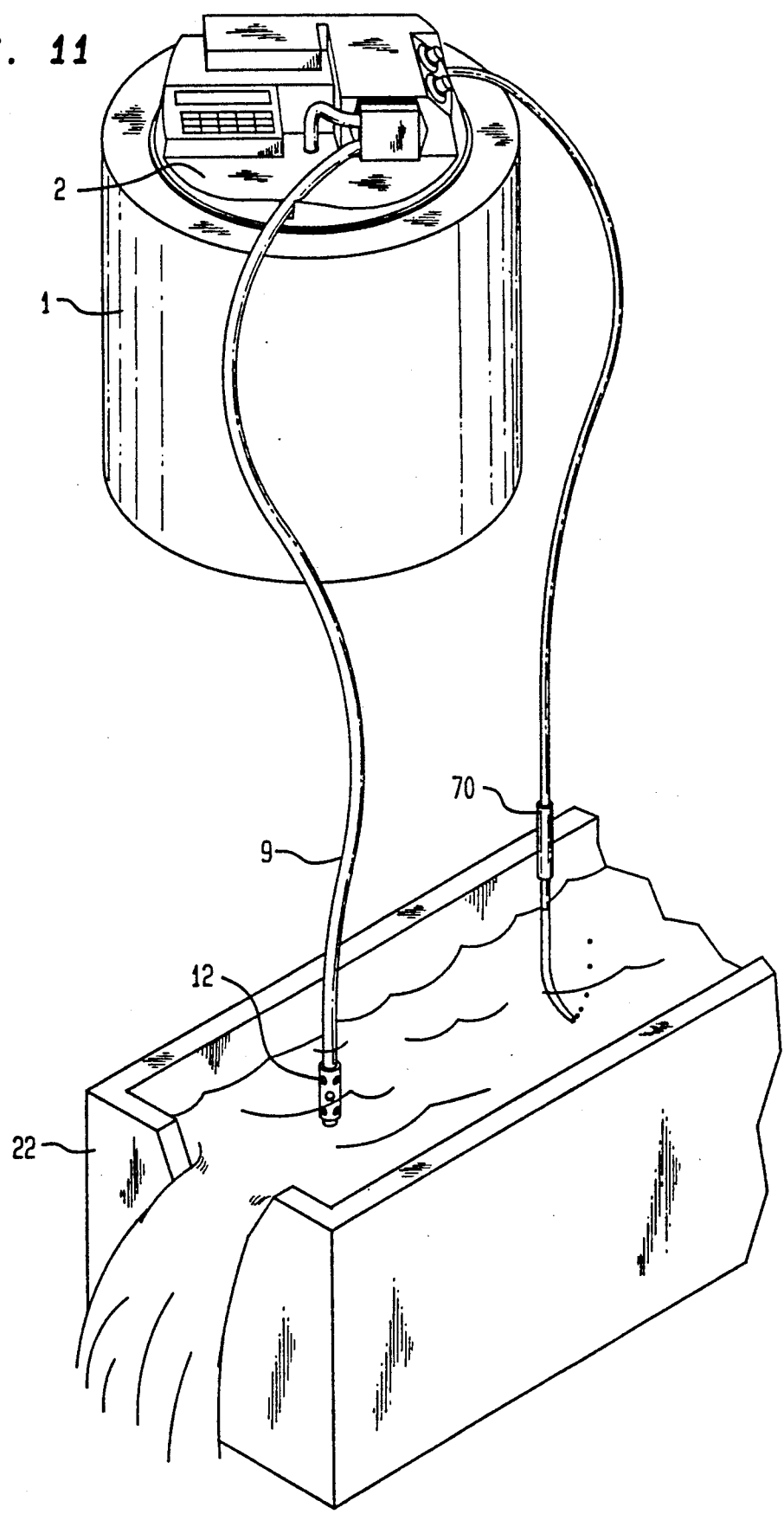
FIG. 11 is a perspective view of the apparatus including a bubbler-type sensing means.

Another alternative type of sensing means is shown in FIG. 11 in the form of a bubbler type sensor 70. The sensor 70 comprises a tube having the outlet end thereof disposed below the fluid surface. An indication of the fluid depth in the channel is obtained by measuring the pressure inside the tube required to maintain a steady stream of air to the outlet thereof. As in the preceding embodiment, suitable interface electronics for sensor 70 are connected with the microprocessor of the apparatus.

Figure 12:
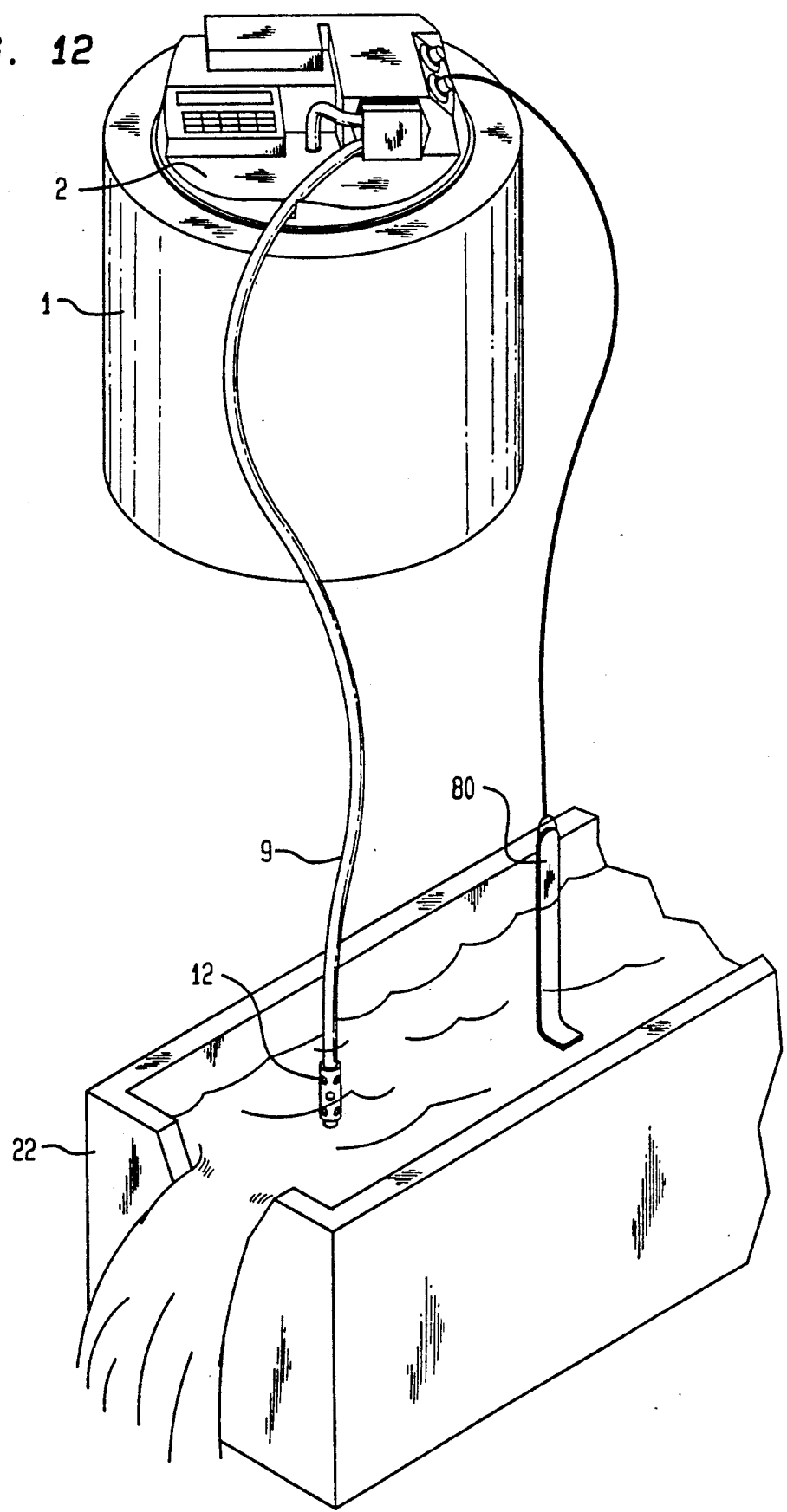
FIG. 12 is a perspective view of the apparatus including a sensing means in the form of a tape with a particular electrical property.

FIG. 12 depicts yet another type of sensing means in the form of a sensor 80 having a predetermined electrical property, such as the capacitance or resistance thereof, which varies according to the sensor area in contact with the fluid in the channel or the length of tape flattened by fluid pressure in the channel. The fluid depth in the channel may be determined by the variation in capacitance or resistance. Hereagain, suitable interface electronics for sensor 80 are connected with the microprocessor.

The invention contemplates that a variety of other sensors may alternatively be employed as the sensing means of the invention, with the interface electronics being modified as needed.

In use, the apparatus according to any of the embodiments of the invention can be conveniently transported to remote sites for mounting in sewer manholes, or to other remote sites for use in other types of applications. When used in a sewer manhole, the apparatus can be conveniently mounted as a single unitary structure above an open flowing sewer passage. The apparatus is mounted for use by: connecting the sensor with one of the connectors 16 and the fluid intake conduit 9 with the pump 8; appropriately mounting the sensor relative to the fluid in the channel; positioning the weighted strainer 12 at the end of conduit 9 within the fluid in the channel; and suspending the unit from the upper end of the manhole (FIG. 5).

The integral unit includes all the electronics, computer programming, and hardware required for fully automatic sampling and flow rate measurement, as well as storage of sampling and flow rate for later retrieval. The unit can be user-programmed to operate according to desired modes of operation, e.g., to collect samples at desired time intervals, after the passage of specified volumes of fluid, or on the basis of some combination of both criteria. The stored data will reflect the time and date of each sample, the flow rate at user-selected intervals, as well as the various other parameters described above. The user can call the data up for display on the alphanumeric display integrally provided on the unit, and/or can transfer the data to a remote output device via the portable data transfer unit. Transfer of the data via the data transfer unit permits recording of the data in a hard copy form via a printer, permanent storage of the data in a database, and/or manipulation of the data for statistical analyses, etc., via a conventional software program.

It will be still further understood that the integral fluid sampling and flow measuring apparatus of the invention may be selectively employed for use for sampling and flow rate measurement both, for sampling only, or for flow rate measurement only, as desired. The independent operation of either the sampling assembly or the flow measuring assembly can be effected via user input to the computer control means according to the invention.

While there have been described hereinabove what are at present considered to be the preferred embodiments of the invention, it will be understood that various modifications may be made therein without departing from the spirit and scope of the invention. The present embodiments are therefore to be considered in all respects as illustrative, and not restrictive. The scope of the invention is indicated by the appended claims rather than by the foregoing description.

We claim:

1. An apparatus for automatically collecting samples from a fluid channel and for measuring a fluid flow-related variable, according to modes of operation selected by a user, said modes of operation including sampling on the basis of time and/or said fluid flow-related variable, comprising:

means for controlling said apparatus;
a fluid sampling assembly having an inlet for receiving fluid from said channel;

power means for supplying power to each element of said apparatus;

said fluid sampling assembly, said control means and said power means comprising an integral operating unit disposed within a single case, said case being sufficiently compact so as to be receivable in a manhole;

said integral operating unit further including at least one input connection for receiving a detected signal related to fluid flow in said channel, and means for conditioning said signal for input to said control means; and said control means comprising a microprocessor, program memory and data memory, wherein:
said program memory stores a plurality of equations for computing values of said fluid flow-related variable;
said data memory stores user-selected input parameters including operating mode selection data, at least one fluid flow-related parameter and sampling times;
said microprocessor receives said signal related to fluid flow from said conditioning means and calculates values of said fluid flow-related variable based on said signal, said at least one user-selected fluid flow-related parameter and a selected one of said stored equations;
said microprocessor controls said fluid sampling assembly according to at least one of said modes of operation selected by the user, based on said user input sampling times and/or computed values of said fluid flow-related variable; and
said data memory stores fluid sampling data and fluid flow-related data.

2. An apparatus according to claim 1, wherein: said at least one user-selected fluid flow-related parameter comprises data relating to the size and type of fluid channel from which fluid samples are collected.

3. An apparatus according to claim 2, wherein: said fluid flow-related variable comprises the fluid depth in said channel.

4. An apparatus according to claim 3, wherein: said fluid flow-related variable further comprises the fluid flow rate in said channel, which is computed by said microprocessor on the basis of said fluid depth.

5. An apparatus according to claim 1, further comprising:
means for selectively transferring said stored data to an external output device; and
said transfer means being controlled by said microprocessor.

6. An apparatus according to claim 1, wherein: said integral operating unit further comprises means for displaying said stored fluid sampling data and fluid flow-related data.

7. An apparatus according to claim 6, wherein: said display means comprises an alphanumeric display mounted to said case so as to be visible to a user; and
said apparatus further comprises user keypad means, mounted to said case and communicating with said data memory, for entering said user-selected input parameters and for retrieving said fluid sampling data and fluid flow-related data stored in said data storage memory by a user command to display said data on said alphanumeric display.

8. An apparatus according to claim 5, wherein:
said integral operating unit further includes an output connection for transferring said fluid sampling data and said fluid flow-related data stored in said data memory;
said transfer means comprises an external portable data transfer unit selectively connectable to said output connection for retrieving said fluid sampling data and fluid flow-related data stored in said data memory; and
said portable data transfer unit is selectively connectable to an external output device for transferring said data to said output device.

9. An apparatus according to claim 7, wherein: said user-selected input parameters entered via said user keypad means further comprise fluid sample collection flow intervals, program start and stop criteria, fluid sample size, sample container selection, and intervals and units for storing fluid flow-related data.

10. An apparatus according to claim 2, further comprising:
sensor means for producing said signal related to fluid flow in said channel when said sensor is mounted in a detecting position relative to said channel, said sensor means being selectively connectable to said at least one input connection of said integral operating unit; and
said at leas one user-selected fluid flow-related parameter further comprising calibration data for said sensor means.

11. An apparatus according to claim 10, further comprising:
a fluid sample intake conduit which extends to fluid in said channel, said sample intake conduit being selectively connectable to said fluid sampling assembly inlet; and
said user-selected input parameters further comprising data relating to the volume of said sample intake conduit and purging thereof.

12. An apparatus according to claim 1, wherein: said data memory is provided with back-up battery power means for permitting said stored fluid sampling data and fluid flow-related data to remain stored in memory when said power means for supplying power to said apparatus is turned off.

13. An apparatus according to claim 1, wherein said fluid sampling assembly comprises:
a pump provided with said inlet for receiving fluid from said channel;
a plurality of sample containers; and
distributor means connected by a conduit with an outlet of said pump for selectively distributing fluid samples to said sample containers.

14. An apparatus according to claim 1, wherein said fluid sampling assembly comprises:
a single fluid sample container disposed in a lower portion of said case.

15. An apparatus for automatically collecting samples from a fluid channel and for measuring fluid flow, according to modes of operation selected by a user, said modes of operation including sampling on the basis of time and/or the fluid flow rate, comprising:
means for controlling said apparatus;
a fluid sampling assembly having an inlet for receiving fluid from said channel;
power means for supplying power to each element of said apparatus;

said fluid sampling assembly, said control means and said power means comprising an integral operating unit disposed within a single case, said case being sufficiently compact so as to be receivable in a manhole;

said integral operating unit further including at least one input connection for receiving a detected signal related to fluid flow in said channel, and means for conditioning said signal for input to said control means; and said control means comprising a microprocessor, program memory and data memory, wherein:

said program memory stores a plurality of equations for computing values of the fluid flow rate;

said data memory stores user-selected input parameters including operating mode selection data, at least one fluid flow-related parameter and sampling times;

said microprocessor receives said signal related to fluid flow from said conditioning means and calculates values of fluid flow rate based on said signal, said at least one user-selected fluid flow-related parameter and a selected one of said stored equations;

said microprocessor controls said fluid sampling assembly according to at least one of said modes of operation selected by the user, based on said user input sampling times and/or computed values of fluid flow rate; and said data memory stores fluid sampling data and fluid flow rate data.

16. An apparatus for automatically collecting samples from a fluid channel and for measuring a fluid flow-related variable, according to modes of operation selected by a user, said modes of operation including sampling on the basis of time and/or said fluid flow-related variable, comprising:

means for controlling said apparatus;

a fluid sampling assembly having an inlet for receiving fluid from said channel;

power means for supplying power to each element of said apparatus;

said fluid sampling assembly, said control means and said power means comprising an integral operating unit disposed within a single case, said case being sufficiently compact so as to be receivable in a manhole;

said integral operating unit further including at least one input connection for receiving a detected signal related to fluid flow in said channel; and said control means comprising a microprocessor, program memory and data memory, wherein:

said program memory is programmed for computing values of said fluid flow-related variable;

said data memory stores user-selected input parameters including operating mode selection data, at least one fluid flow-related parameter and sampling times;

said microprocessor receives said signal related to fluid flow via said input connection and utilizes said program memory to calculate a value of said fluid flow-related variable based on said signal and said at least one user-selected fluid flow-related parameter;

said microprocessor controls said fluid sampling assembly according to at least one of said modes of operation selected by the user, based on said user input sampling times and/or computed values of said fluid flow-related variable; and said data memory stores fluid sampling data and fluid flow-related data.

17. An apparatus according to claim 16, wherein:
said at least one user-selected fluid flow-related parameter comprises data relating to the size and type of fluid channel from which fluid samples are collected.

18. An apparatus according to claim 16, wherein:
said fluid flow-related variable comprises the fluid depth in said channel.

19. An apparatus according to claim 18, wherein:
said fluid flow-related variable further comprises the fluid flow rate in said channel, which is computed by said microprocessor on the basis of said fluid depth.

20. An apparatus according to claim 16, further comprising:
means for selectively transferring said stored data to an external output device; and
said transfer means being controlled by said microprocessor.

21. An apparatus according to claim 16, wherein:
said integral operating unit further comprises means for displaying said stored fluid sampling data and fluid flow-related data.

22. An apparatus according to claim 21, wherein:
said display means comprises an alpanumeric display mounted to said case so as to be visible to a user; and
said apparatus further comprises user keypad means, mounted to said case and communicating with said data memory, for entering said user-selected input parameters and for retrieving said fluid sampling data and fluid flow-related data stored in said data storage memory by a user command to display said data on said alphanumeric display.

23. An apparatus according to claim 20, wherein:
said integral operating unit further includes an output connection for transferring said fluid sampling data and said fluid flow-related data stored in said data memory;
said transfer means comprises an external portable data transfer unit selectively connectable to said output connection for retrieving said fluid sampling data and fluid flow-related data stored in said data memory; and
said portable data transfer unit is selectively connectable to an external output device for transferring said data to said output device.

24. An apparatus according to claim 22, wherein:
said user-selected input parameters entered via said user keypad means further comprise fluid sample collection flow intervals, program start and stop criteria, sample size, fluid sample container selection, and intervals and units for storing fluid flow-related data.

25. An apparatus according to claim 17, wherein:
sensor means for producing said signal related to fluid flow in said channel when said sensor is mounted in a detecting position relative to said channel, said sensor means being selectively connectable to said at least one input connection of said integral operating unit; and
said at least one user-selected fluid flow-related parameter further comprising calibration data for said sensor means.

26. An apparatus according to claim 25, wherein:
a fluid sample intake conduit which extends to fluid in said channel, said sample intake conduit being selectively connectable to said fluid sampling assembly inlet; and
said user-selected input parameters further comprising data relating to the volume of said sample intake conduit and purging thereof.

27. An apparatus according to claim 16, wherein:
said data memory is provided with back-up battery power means for permitting said stored fluid sampling data and fluid flow-related data to remain stored in memory when said power means for supplying power to said apparatus is turned off.

28. An apparatus according to claim 16, wherein said fluid sampling assembly comprises:
a pump provided with said inlet for receiving fluid from said channel;
a plurality of sample containers; and
distributor means connected by a conduit with an outlet of said pump for selectively distributing fluid samples to said sample containers.

29. An apparatus according to claim 16, wherein said fluid sampling assembly comprises:
a single fluid sample container disposed in a lower portion of said case.

30. An apparatus according to claim 16, wherein:
said program memory stores a plurality of equations for computing values of said fluid flow-related variable in said channel; and
said microprocessor receives said signal related to fluid flow via said input connection and calculates values of said fluid flow-related variable based on said signal, said at least one user-selected fluid flow-related parameter, and a selected one of said equations stored in said program memory.

31. An apparatus according to claim 16, wherein:
said integral operating unit further comprises means for conditioning said signal for input to said control means.

32. A method for automatically collecting samples from a fluid channel and for measuring a fluid flow-related variable, according to modes of operation selected by a user, said modes of operation including sampling on the basis of time and/or said fluid flow-related variable, comprising the steps of:
connecting, to an input connection of an integral operating unit, a sensing means for producing a signal related to the fluid flow in said channel;
connecting a sample intake conduit to an inlet of a sampling assembly of said integral operating unit;
mounting said sensing means in a detecting position relative to said channel;
lowering a lower intake end of said conduit into fluid in said channel;
positioning in an operable position said integral operating unit, including said fluid sampling assembly, means for supplying power to said integral operating unit, and means for controlling said integral operating unit, all disposed within a single case which is sufficiently compact so as to be receivable in a manhole;
operating said control means, including program memory thereof programmed for computing values of said fluid flow-related variable, data memory thereof which stores user-selected input parameters including operating mode selection data, at least one fluid flow-related parameter and fluid sampling times, such that a microprocessor of said control means receives said signal from said sensing means via said input connection and utilizes said program memory to calculate the value of said fluid flow-related variable based on said signal and said at least one user-selected fluid flow-related parameter, for controlling said fluid sampling assembly according to at least one of said modes of operation selected by the user, based on said user input sampling times and/or computed values of said fluid flow-related variable; and
operating said data memory of said control means for automatically storing sampling data and fluid flow-related data.

33. A method according to claim 32, further comprising the step of:
displaying said stored fluid sampling data and fluid flow-related data on an alphanumeric display of said integral operating unit, in response to a user display input command.

34. A method according to claim 32, further comprising the step of:
retrieving said stored fluid sampling data and fluid flow-related data via a portable data transfer unit by connecting said data transfer unit to an output connection of said integral operating unit and inputting a command to transfer said data to said transfer unit; and
transferring said data retrieved by said portable data transfer unit to an external output device by connecting said data transfer unit to said external output device.

35. A method according to claim 32, further comprising the step of:
inputting user commands, via a user input keypad means of said integral operating unit, relating to sampling parameters including sample collection time intervals, sample collection flow intervals, program start and stop criteria, and sample size; and
inputting user commands, via said keyboard means, relating to fluid flow-related parameters including specifications relating to said fluid channel, and intervals and units for storing fluid flow-related data.

36. A method according to claim 32, wherein:
when said control means is operated to control said fluid sampling assembly, said microprocessor of said control means receives said signal from said sensing means via said input connection and utilizes a selected one of a plurality of equations stored in said program memory for computing values of said fluid flow-related variable based on said signal and at least one user-selected fluid flow-related parameter.

* * * * *

UNITED STATES PATENT AND TRADEMARK OFFICE
CERTIFICATE OF CORRECTION

PATENT NO. : 5,091,863

DATED : February 25, 1992

INVENTOR(S) : William G. Hungerford, Donald Miller, Carl Griffith, Donald Kaiser It is certified that error appears in the above-identified patent and that said Letters Patent is hereby corrected as shown below:

Column 5, line 45, change "FIG. 1" to -- FIG. 2 --.
Column 8, line 3, change "under" to -- until --;
          line 41, change "fluid" to -- the fluid --;
          line 43, after "rate" insert -- which is calculated --.
Column 9, line 2, change "for" to -- of --;
          line 19, delete "is".
Column 12, line 24, after "rate" insert -- data --.
Column 14, line 29, change "leas" to -- least --.
Column 16, line 29, change "alpanumeric" to -- alphanumeric --;
               59, change "wherein" to -- further comprising --.
Column 17, line 1, change "wherein" to -- further comprising --.

Column 8, lines 42 and 43, change "to calculate the" to read --the fluid--.

Signed and Sealed this

Sixth Day of July, 1993

*Attest:*

MICHAEL K. KIRK

*Attesting Officer*     Acting Commissioner of Patents and Trademarks